United States Patent [19]
Gimeno

[11] Patent Number: 5,004,460
[45] Date of Patent: Apr. 2, 1991

[54] NON-REUSABLE SYRINGE

[76] Inventor: Carlos V. Gimeno, Lorenzo Carbonell, 03003 Alicante, Spain

[21] Appl. No.: 241,382

[22] Filed: Sep. 7, 1988

[30] Foreign Application Priority Data

Jan. 7, 1988 [ES] Spain ................................. 8800026

[51] Int. Cl.$^5$ .............................................. A61M 5/00
[52] U.S. Cl. ..................................... 604/228; 604/110
[58] Field of Search ................ 604/110, 192, 208, 218, 604/228; 128/655; 222/386

[56] References Cited

U.S. PATENT DOCUMENTS

| | | | |
|---|---|---|---|
| 2,130,305 | 9/1938 | Lewis | 604/218 |
| 3,320,954 | 5/1967 | Cowley | 604/110 |
| 4,220,151 | 9/1980 | Whitney | 604/110 |
| 4,675,005 | 6/1987 | DeLuccia | 604/110 |
| 4,677,980 | 7/1987 | Reilley et al. | 604/228 |
| 4,699,614 | 10/1987 | Glazier | 604/228 |
| 4,775,363 | 10/1988 | Sandsdalen | 604/110 |
| 4,775,364 | 10/1988 | Alles | 604/110 |
| 4,810,249 | 3/1989 | Haber et al. | 604/210 |

FOREIGN PATENT DOCUMENTS

| | | | |
|---|---|---|---|
| 0308380 | 12/1987 | European Pat. Off. | 604/110 |
| 88/10127 | 12/1988 | PCT Int'l Appl. | 604/110 |
| 89/04185 | 5/1989 | PCT Int'l Appl. | 604/110 |

OTHER PUBLICATIONS

Abstract of Spanish Utility Model No. 229607, Industrial Patent Abstracts (Spain), Sep. 1, 1977, pg. 6389.

Primary Examiner—John D. Yasko
Assistant Examiner—Adam J. Cermak
Attorney, Agent, or Firm—Kuhn and Muller

[57] ABSTRACT

A non-reusable hypodermic syringe consists of a barrel and a plunger, the plunger having first and second sections divided by a torque reacting point of rupture between them. Means is provided for causing relative rotation between one of the plunger sections and the barrel during the ejection cycle so as to create a torque differential between the sections which results in a rupture of the plunger at the torque reacting point at the end of the ejection cycle. A clutch mechanism is provided to disengage rotational motion from the plunger when liquid is being drawn into the barrel. The clutch engages or transmits rotational motion to the plunger when the plunger is moved in the other direction to eject liquid from the barrel.

13 Claims, 4 Drawing Sheets

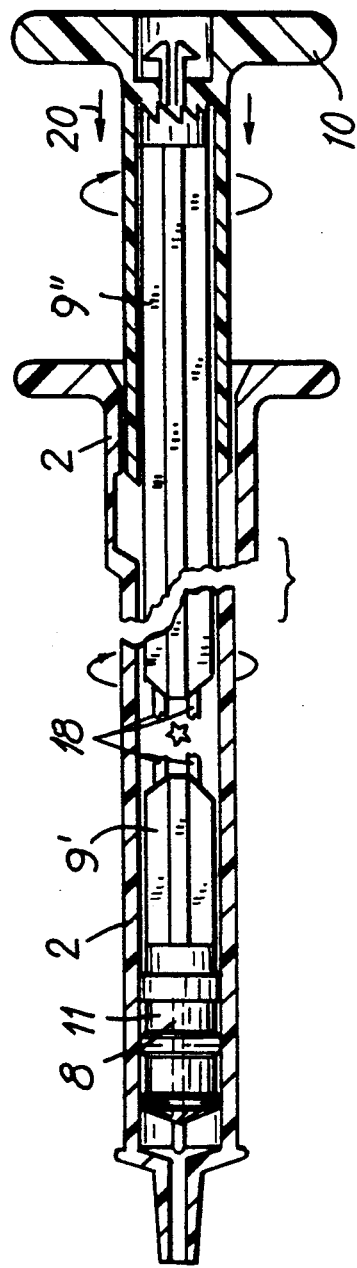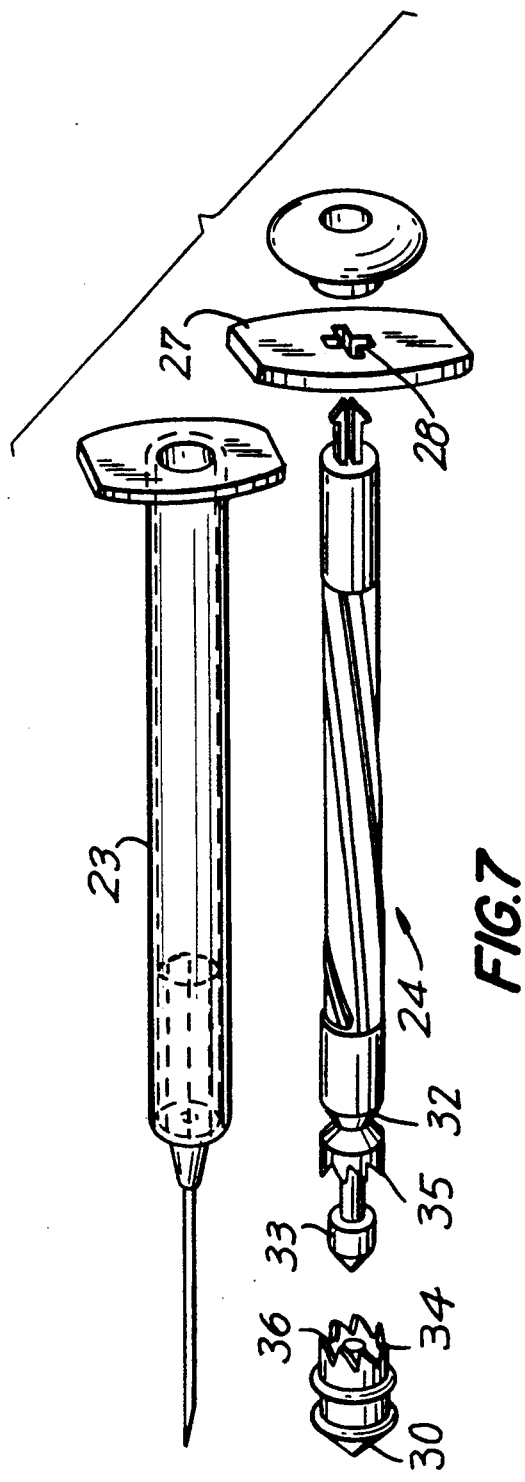

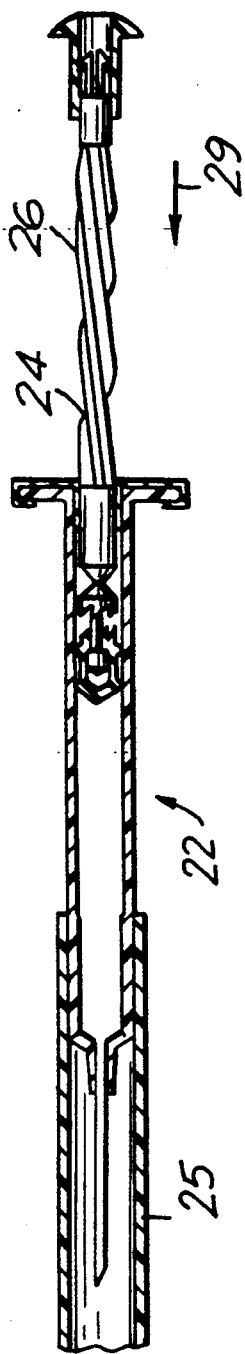
FIG.8
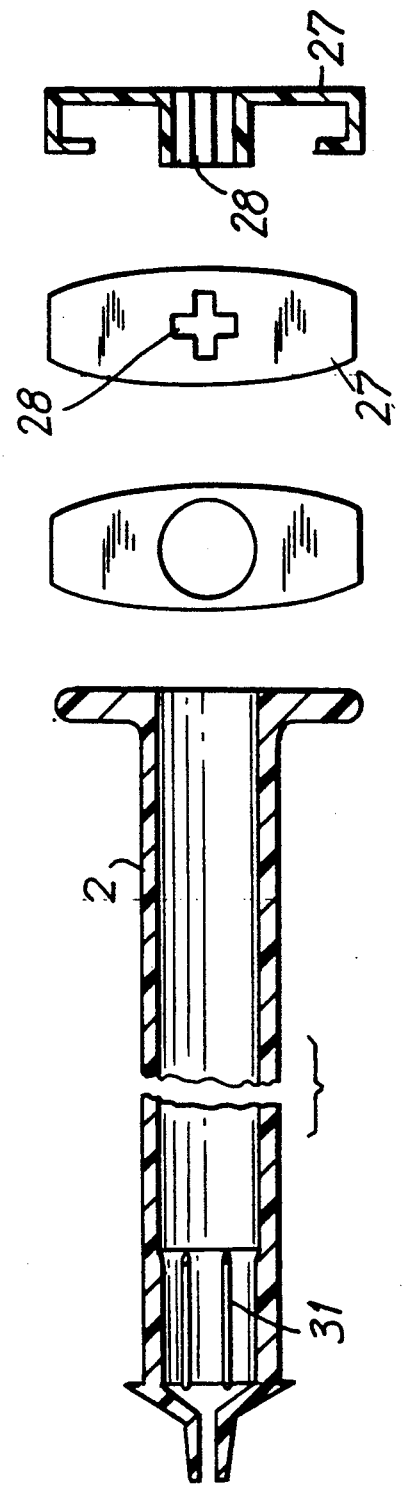
FIG.9a  FIG.9b  FIG.9c
FIG.9

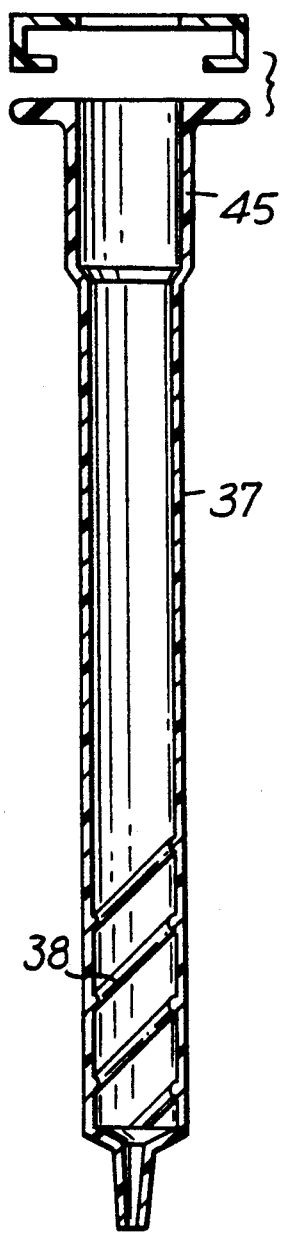
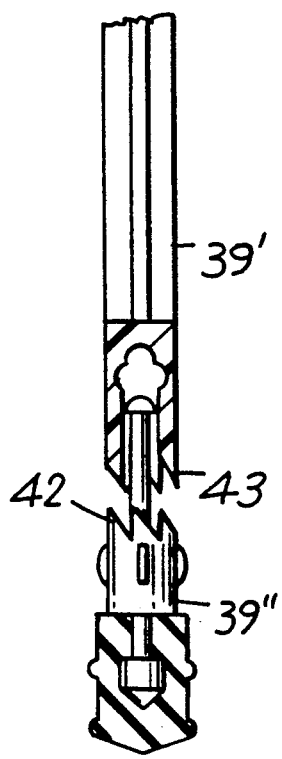
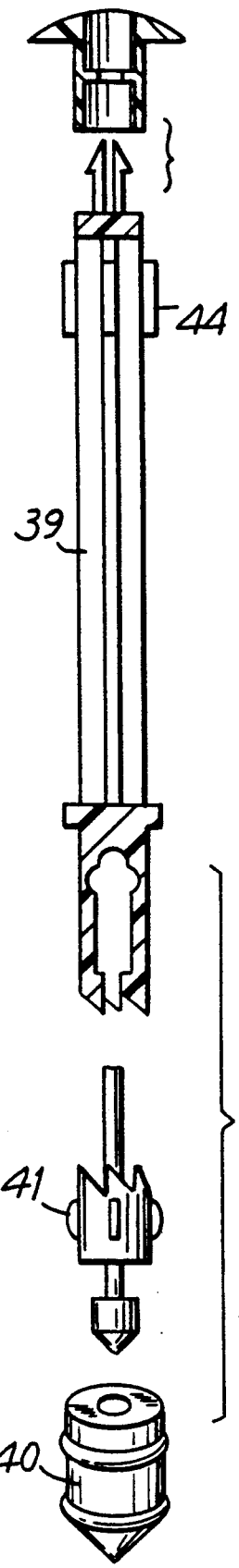

NON-REUSABLE SYRINGE

FIELD OF THE INVENTION

This invention relates to hypodermic syringes and more particularly to a self-destructible syringe that renders itself un-reusable after a single use.

BACKGROUND OF THE INVENTION

There are already low cost disposable syringes made of plastic materials, such as polypropylene and the like, which have replaced almost completely the older ones made of glass, thus eliminating the sterilization problems that the older type used to have.

Nevertheless, since this type of syringe retains all its functional characteristics after use, except of course for not being sterile, their being disposable depends only on the will of the user and for this reason they are not strictly single use, since they may be re-utilized by un-scrupulous users.

The huge health problem posed by spreading infectious diseases by this means is well known, and the increase in dangerous diseases like viral hepatitis and acquired immune deficiency syndrome (AIDS) in persons that share and reuse syringes is a particularly troublesome problem. This means of contamination, however, is not limited exclusively to unscrupulous users who re-utilize syringes; accidental punctures among health professionals are very common, caused by the needles of syringes that have already been used with patients.

There have been other attempts heretofore to ameliorate the aforementioned problems. There is a disposable syringe that can be rendered unusuable after its use through the voluntary rupture of the stem of its plunger, as represented by the Spanish Utility Model No. 229607 granted to DEXA, S.A. Hypodermic syringes with sheaths for protection of the needle are also known.

Nevertheless, the solutions known up to now do not guarantee the resolution of the aforesaid problems. Concerning un-reusability after use of the hypodermic syringe in the Spanish model of the DEXA, S.A. company aforementioned, it is a syringe the plunger part of which comprises a stem that may be ruptured due to a weakening in the material of said stem, so that the syringe will be rendered unusable only depending on the will of the user, that is to say, it may be rendered permanently unusable provided the user so desires and takes the necessary action, and this evidently does not happen with unscrupulous users such as drug addicts.

The solution is no more valid concerning protection against accidental punctures as known at present, and which consists of fitting these syringes with sheaths wrapped around the needle. As now given, this protective sheath will guarantee the asepsis of the needle while the preliminary operations of preparation of the solution to be rejected are carried out, therefore accidental punctures are not prevented this way.

Thus, it is the aim of this invention to provide a hypodermic syringe of the above-mentioned type, that is to say, on the basis of low cost materials which will make them "disposable" and which render themselves irreversibly un-reusable during the action of injecting, that is to say, without the intervention of the will of the user in the process of rendering themselves un-reusable, so that a truly "single use" syringe is provided.

Additionally, it is one of the aims of the invention to provide a syringe of this type that has a device for protection of the needle, so as to eliminate or at least decrease the possibility of accidental punctures with the needle.

With this invention such aims are attained since this syringe, having plunger and barrel portions with a plunger stem that has a rupture point located near its distal end, is provided with the following:

Means for turning placed in a cooperating manner on the aforesaid plunger and/or barrel parts so that when the plunger moves forward during the injection it causes the relative turning of said portions;

Means for blocking the turn of the stem placed in a cooperating manner on the inner wall of the said barrel and/or plunger parts that prevent the simultaneous or solidary turning of the two sections of the plunger stem located on either side of the point or line of rupture, so that as the plunger moves during the injection there is between the two sections of the stem sufficient torque to cause the rupture of the stem at this rupture point; and Means for coupling, acting like a clutch, located at either end of the stem of the plunger section, which with the backward or upward motion of the plunger stem during the suction of the substance to be injected, uncouple the aforementioned means for turning the stem in such a way that the aforesaid turning motion does not take place. The torque is thereby eliminated and consequently the stem does not rupture during the loading of the syringe.

In an embodiment of the invention, the means for turning the plunger stem consists of a part coaxially coupled to the upper part of the plunger stem on whose periphery there are longitudinal fillets cooperating with helicoidal grooves made in the inner wall of the upper part of the barrel section. In this embodiment the means for blocking consists of longitudinal fillets placed on the inside wall of the distal end of the barrel section of the syringe, adjacent to the end part of the stem, i.e., the plunger itself which as is well known, is normally made of some elastic material such as rubber. Thus, the turning of this section of the stem is prevented, since the rubber part cannot slide over the aforementioned fillets.

In this embodiment, the means for coupling is a fleam tooth clutch consisting of indentations placed in a complementary position at the upper end of the stem and on the aforesaid part coaxial with it that determines the means for turning. As will easily be understood by those skilled in the art, in order to achieve the uncoupling of the aforesaid clutch during the backward motion of the plunger stem in the course of the suction of the solution to be injected, it is necessary that there be some play between the longitudinal fillets of the aforesaid coaxial part and the helicoidal grooves located on the upper inner wall of the barrel. Furthermore, between the plunger stem and the part coaxially coupled to it there must also be some longitudinal play.

In another embodiment of the invention the means for causing the rotation of the plunger stem will be located on the lower or distal section of the syringe in the form of helicoidal grooves made in the inner wall of the barrel and cooperating with the longitudinal fillets of the distal or lower end of the plunger stem. In this case, the means for blocking the turn will consist of grooves and cooperating fillets located on the upper part of the stem and upper inner wall of the barrel part. For this embodiment the means for coupling, also in the form of a fleam tooth clutch, must be located near the end of the plunger stem.

In another embodiment of the invention the means for causing the turning of the stem are constituted jointly by a plunger stem having the configuration of a screw and a guiding piece coaxially coupled to it, with a cruciform opening, so that the stem is forced to turn as it goes through the cruciform opening. In this embodiment, the means for blocking the turn of the stem are also made up by fillets on the inner wall of the syringe barrel which brush against the rubber plunger. In this case too, the means for coupling that allow the backward or upward motion of the plunger stem during the suction of the substance to be injected consists of a fleam tooth clutch located on the lower part of the plunger stem.

BRIEF DESCRIPTION OF THE DRAWINGS

Other characteristics and advantages of the invention will be more clearly appreciated from the following description, made with the help of attached drawings, related to non-limiting examples of the preferred embodiment, where:

FIG. 2a is a top cross-sectional view of FIG. 2.

FIGS. 5 and 6 are partial sectional views related to the functioning of the syringe as per FIG. 1;

FIG. 7 shows a breakdown view of a syringe as per another embodiment of the invention;

FIGS. 8, 9, 9a, 9b and 9c show details of a syringe as per the embodiment of FIG. 7; and FIGS. 10 through 12 show views related to a syringe as per a third embodiment of the invention.

BRIEF DESCRIPTION OF THE PREFERRED EMBODIMENTS

Figure 1:
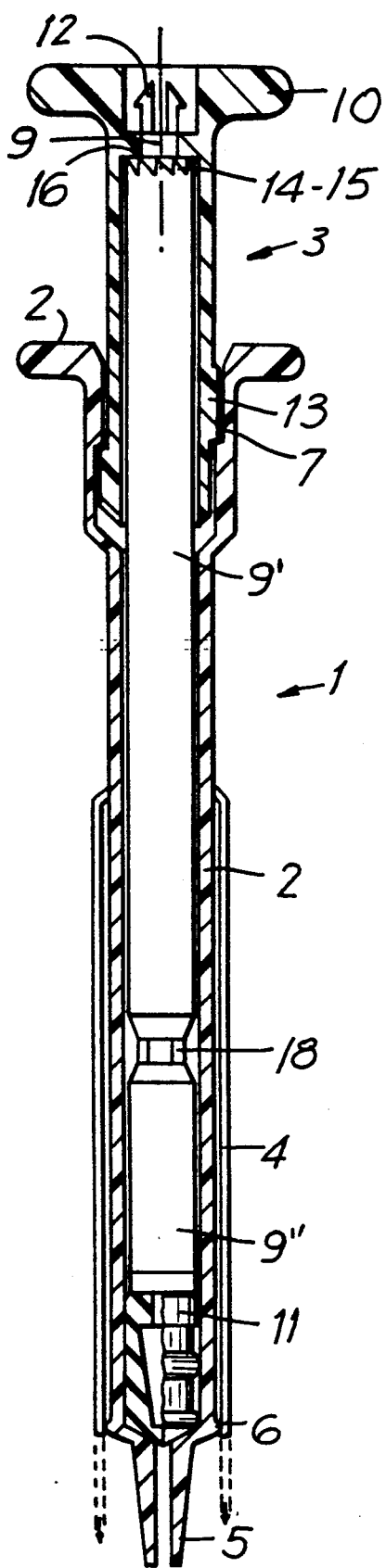
FIG. 1 is a partial sectional view which illustrates a hypodermic syringe made in accordance with the invention.
Figure 2:
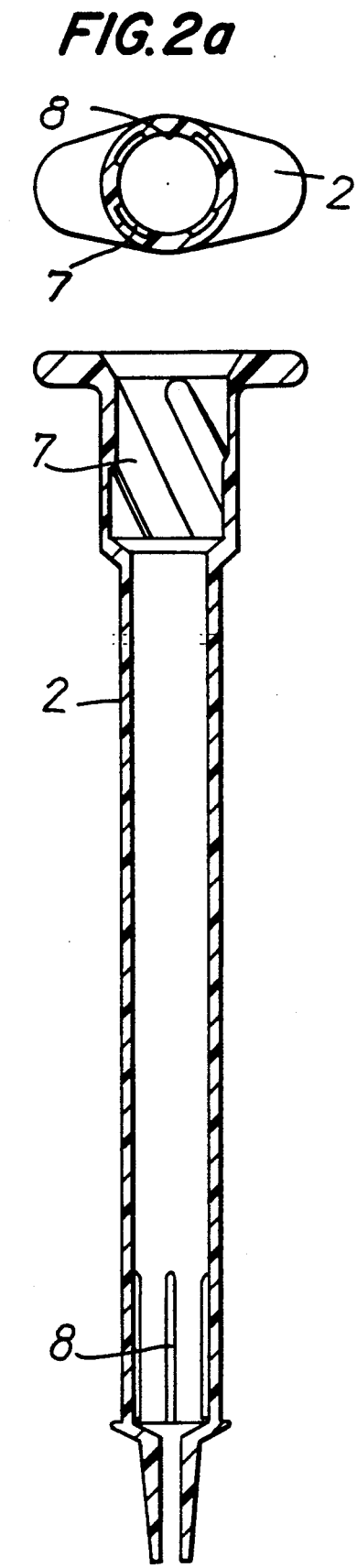
FIGS. 2 through 4 show partial sectional views of a syringe as per FIG. 1.
Figure 3:
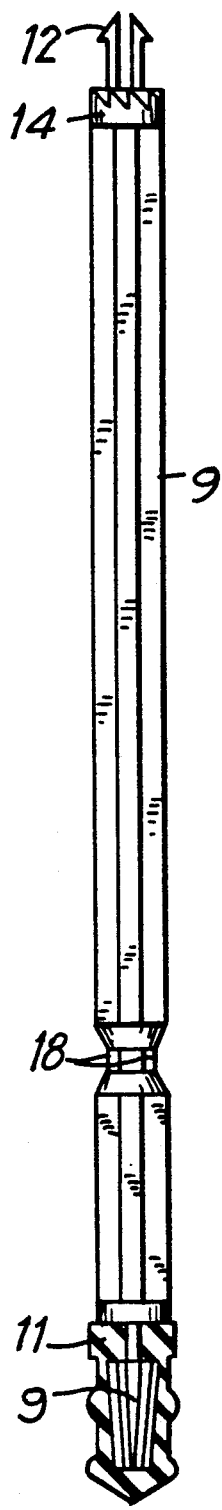
Figure 4:
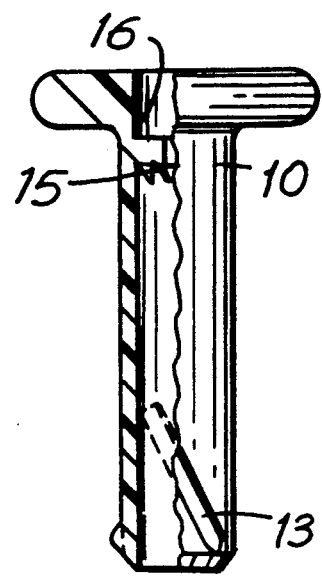

In reference to FIGS. 1 through 4, it may be observed that the syringe 1, as it has been presented, comprises a barrel part 2 and a plunger part 3. Additionally, there is on the outside of the barrel part 2 coaxial with and sliding on it, a tubular part 4, in the guise of a protecting sheath or hood, so that the needle 5 may be hidden by simply sliding the aforesaid tubular part 4 up to the stops 6 located on the outside of the barrel part 2 of syringe 1.

The barrel part 2 has in its inner wall, at its upper end, some slanting grooves 7 in the form of helicoidal threads, while at its other end and also on the inner wall, there are some longitudinal ridges or fillets 8.

The plunger part consists of the stem 9 and the push handle 10, coupled in the manner to be described in detail below. Stem 9 has mounted on its distal end a plunger 11, conventionally made of rubber or similar material, while its other end consists of an insertable end in the form of a centrally slotted stub. Additionally, as it has been stated, there is a point or line of rupture 18 in the stem 9 near its distal end, so that two sections 9' and 9" are formed on either side of such point or line of rupture. The push handle 10, which is capable of being coaxially coupled to the stem 9, has on its lateral surface some straight ridges or fillets 13, cooperating with the helicoidal grooves or striations 7, located on the aforesaid barrel 2 part.

Additionally, at the upper end of stem 9 there are certain indentations 14, which are complementary of another group of indentations 15 located inside the push handle 10. The aforesaid push handle 10 has on its upper part an internal lodging 16 for the coupling of the stub 12 of stem 9. This way, a coupling or clutch between stem 9 and push handle 10 is determined which will allow the solidary turn of these parts around axis 17, clockwise, while uncoupling will result from a turn in the opposite direction.

In reference now to FIGS. 5 and 6, the functioning of syringe 1 will be described.

Figure 5:
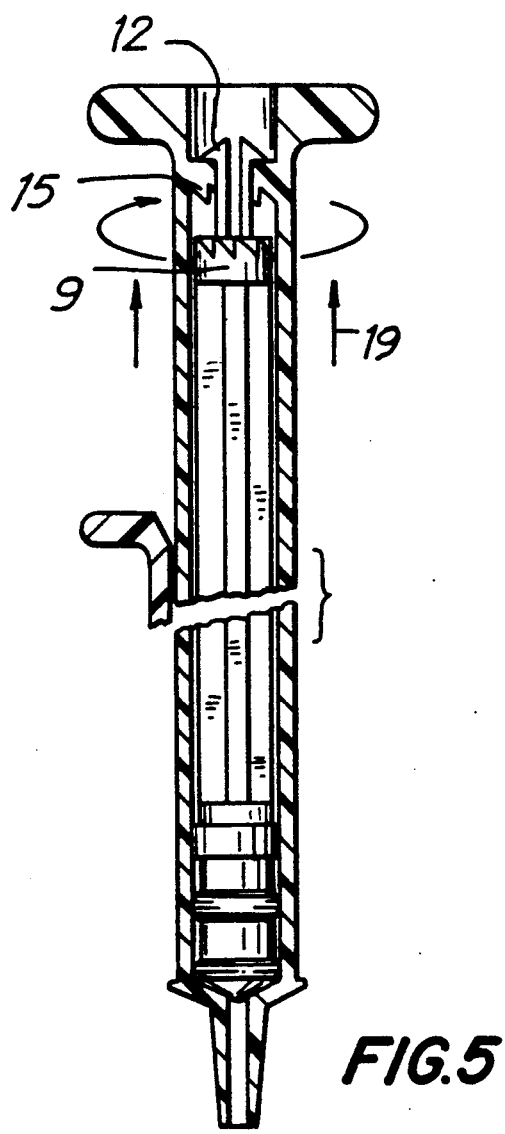

In the first place and making special reference to FIG. 5, it can be observed that suction of the injectable substance with syringe 1 will result, as is usual, from the withdrawal of the push handle 10 in the direction of the arrows 19, so that stem 9 is drawn back without any turn. Thus, the injectable solution at the entry point into syringe 1 will be drawn towards the barrel part 2. Due to indentations 14 and 15, located respectively at the end of the stem 9 and inside push handle 10, as well as to the play allowed between the helicoidal grooves 7 of the barrel part 2 and the longitudinal fillets 13 of push handle 10, stem 9 by means of its ending 12 is pulled backward by push handle 10 without any turning component whatsoever.

In contradistinction, and making special reference to FIG. 6, it will be observed that for impulsion, during the acting of injecting, the procedure is the usual one, the application on push handle 10 of a force following arrows 20 so that indentations 14 and 15, which are respectively located at the extreme end of stem 9 and inside push handle 10 will be coupled or inserted. In this way, the pressure exerted on push handle 10 is transmitted to the stem 9. If this pressure continues in this direction of the arrows 20, the fillets 13 of handle 10 will be forced to move along the helicoidal grooves 7 of the barrel part 2, resulting in a combined forward and clockwise turning motion of the stem-handle combination 9-10 and the consequently forward and clockwise turning motion of plunger 11 located at the end of stem 9. It will be evident to those skilled in the art that as long as a force is applied in the direction of the arrows 20, stem 9 and push handle 10 will form a solidary whole as far as turning is concerned due to the coupling of the indentations 14 and 15 located on the aforesaid parts which behave like a fleam tooth clutch. As handle 10 is pushed further, there is a consequent advance of plunger 11 which is affixed to stem 9 so that that part will reach the inner area of barrel 2 where the longitudinal fillets 8 are located. At this point, and given the resistance to the slipping of plunger 11 over said fillets 8, the turning of said plunger 11 will be prevented since plunger 11 is solidary with stem 9. Between portions 9' and 9" of the stem, torque is generated which is applied at rupture point 18 and will cause the rupture of the stem. As those skilled in the art will easily understand, the rupture point 18 has predetermined dimensions such that it will break when the plunger 11 has reached the bottom of the barrel 2. Thus, all of the injectable substance in the syringe may be injected.

In relation to FIGS. 7 through 9, there is shown another embodiment of the invention. In the alternate embodiment, the hypodermic syringe 22, which has an analogous configuration, has parts of the barrel 23 and a plunger 24. There is also a sheath or hood 25, coupled in a sliding manner to the barrel part 2 in order to cover the needle of the syringe.

In this case, the forward motion and the clockwise turning motion of the stem 24 is achieved through the interaction of a helicoidal thread 26 on the central portion of stem 24 with guiding part 27 and a cruciform slot 28, through which said fillet 26 must move. Thus, as the stem 24 is pushed in the direction of the arrow 29, there is a combined forward and turning motion of the plunger 30 which is fixed solidary with the distal end of said stem 24. Its turning motion will be prevented by friction. When said plunger 30 reaches the fillets 31, which are located in a corresponding manner inside the extreme end of barrel 23, torque is created which is applied at the rupture point 32 thereby causing its rupture. In this case, too, the resistance of the rupture point 32 has been calculated in such a way that it will break just when plunger 31 reaches the extreme end of the barrel 23, so that all of the substance in the barrel of the syringe may be injected.

In this embodiment the backward motion of the stem 24, for suction of the injectable substance, can proceed without rupture of the rupture point 32. This is due to the coupling located between plunger 30 and the distal end 33 of stem 34. Plunger 30 and stem 24 move in solidarity when pulled due to the existing coupling between end 33 of stem 24 and hole 34 of plunger 30. Insofar as turning motion is concerned, plunger 30 and stem 24 are also solidary in a clockwise motion and independent if motion is counterclockwise. This is due to indentations 35 and 36 which are located in corresponding positions on the end of stem 24 and on plunger 30.

In reference now to FIGS. 10 through 12, related to an alternative embodiment of the invention, the syringe likewise consists of a barrel part 37 on the walls of whose distal end there are slanting grooves 38 in the form of helicoidal threads and a stem 39 carrying a plunger 40.

In this case, when stem 39 is pushed in the course of administering the injection, it will move inside barrel 37 in a straight line without any turning component whatsoever. When plunger 40 reaches the grooved portion 38 of barrel 2 certain fillets 41 located on said plunger 40, will become inserted in the aforesaid grooves 38 giving a clockwise turning motion to the whole of the stem. This is due to the coupling of indentations 42 and 43, located in a complementary manner on the two sections of the stem 39' and 39''. Contrarywise, the upper part 39' of stems 39 is prevented from turning due to the coupling of certain longitudinal fillets 44 of the upper part of plunger 39 with grooves 45, which are also longitudinal and located on the inner wall of the upper end of barrel 37. The torque thus generated between sections 39' and 39'' of the stem will cause stem 39 to break through a rupture point or line (not shown) which is included in the stem. In this embodiment, the upward motion of stem 39 causing suction of the injectable substance into the syringe is due to the solidary coupling for purposes of pulling between plunger 40 and the stem 39 as it has been described for the previous embodiment.

As those skilled in the art will understand, the shape and location of the grooves, fillets, coupling of stem and plunger, etc., may have equivalent mechanical solutions, the only important thing being according to the invention the creation of torque between the two sections the stem. In this way, the rupture of the stem is effectively caused at the corresponding rupture point, thus rendering the syringe useless for a second use when the plunger reaches the extreme end of the barrel for the total ejection of the injectable substance. As has been shown in the aforegoing descriptions, it follows, likewise, that the coupling in the form of a clutch that may be uncoupled by pulling on or backward motion of the stem may be located either on the upper or on the lower part of the stem, the only thing that matters in this case is that uncoupling result from the backward motion of the stem.

Therefore, such resulting embodiments or others which are not fundamentally derived from routine experimentation on the objects of the invention shall be considered included within the field and scope of the same.

What is claimed is:

1. A single use self-destructible syringe having a barrel part defining a longitudinal axis and plunger part with a plunger stem having a rupture point, the plunger stem being adapted to move forward and backward relative to the barrel part, characterized in that the syringe comprises:

Means for turning said plunger part relative to said barrel part during forward motion of said plunger part defining the action of injecting;

Means for blocking the turning of one segment of the plunger stem on one side of the rupture point as the plunger part advances during the action of injecting so that sufficient torque is generated between said one segment and the remainder of the stem to break said stem at said rupture point at the end of the injecting action; and Clutch means on one end of the plunger stem, for coupling said turning means to the plunger stem during the action of injecting and for uncoupling said turning means from the plunger stem during the backward movement thereof so as to prevent turning of said plunger stem thereby to avoid breaking of the plunger stem at the rupture point during the loading of the syringe.

2. A syringe according to claim 1, whereby the means for turning the plunger stem comprises a push handle coupled coaxially to one end of said stem on the periphery of which push handle are located one or more fillets extending longitudinally of said push handle and acting in cooperation with a helicoidal groove formed in the inner wall of the barrel part.

3. A syringe according to claim 2, characterized in that said blocking means comprises a plurality of fillets protruding radially from and extending longitudinally along the inner wall of the barrel part substantially adjacent and contacting said one segment of the plunger stem in such a manner that as said one segment of the stem advances said fillets exert friction on said one segment and thereby prevent its turning.

4. A syringe according to claim 3, wherein said coupling means comprises, engaging means for translating rotational movement of said push handle to said plunger stem when said push handle is moved forward in said barrel part, and engaging means for transmitting only non-rotational movement of said push handle to said plunger stem when said push handle is moved backward in said barrel part.

5. A syringe according to claim 2, characterized in that said fillets of the push handle and said helicoidal groove in the wall of the barrel part present some relative play.

6. A syringe according to claim 1, characterized in that said turning means comprises a guide member coupled to one end of the barrel part and having a cruciform slot engaging a helicoidal thread cut in said stem.

7. A syringe according to claim 6, characterized in that said blocking means comprising fillets on the inner wall of the barrel part adjacent the forward end thereof and engageable with said plunger part to exert friction on said plunger part thus preventing said plunger part from turning.

8. A syringe according to claim 7, characterized, in that said coupling means comprises indentations on the plunger part adjacent the forward end of the stem, said plunger and stem being coupled for purposes of backward movement thereof by insertable parts.

9. A syringe according to claim 1, characterized in that said turning means comprises a helicoidal groove located in the inner wall of the barrel part at the forward end thereof and cooperating with fillets located in a corresponding position on the plunger.

10. A syringe according to claim 9, characterized in that said blocking means comprises grooves extending longitudinally along the inner wall of the barrel part and cooperating with fillets extending longitudinally along the stem.

11. A syringe according to claim 10, characterized in that said coupling means comprises indentations in the plunger and the stem where said plunger and stem are coupled for purposes of pulling through insertable endings.

12. A syringe according to claim 1, comprising a protecting sheath slidably mounted coaxially on the outside of the barrel part.

13. A non reusable hypodermic syringe comprising a barrel and a plunger, said plunger having a first section and a second section, a torque reacting point of rupture between and connecting said first and second sections, means for causing relative rotation between one of said sections and said barrel, means for preventing relative rotation between the other of said sections and said barrel, thereby creating increasing torque differential between said sections during movement of said plunger, a clutch mechanism between the ends of said plunger, said clutch being disengaged when said plunger is moved in a first direction to draw liquid into said barrel, whereby there is no relative rotation between said first and second sections of said plunger, said clutch being engaged when said plunger is moved in the other direction to eject liquid from said barrel, whereby there is relative rotation between said first and sections of said plunger causing rupture of said torque reacting point substantially at the end of the ejecting stroke of said plunger, thereby separating said sections of said plunger.

* * * * *